United States Patent

Miyagawa et al.

[11] Patent Number: 6,002,656
[45] Date of Patent: *Dec. 14, 1999

[54] DEVICE FOR INSPECTING THE SURFACE OF DISC-SHAPED RECORDING MEDIUM

[75] Inventors: Akira Miyagawa; Hironori Fujita, both of Kanagawa, Japan

[73] Assignees: Sony Corporation; Sony Chemicals Corp, both of Japan

[*] Notice: This patent is subject to a terminal disclaimer.

[21] Appl. No.: 08/464,377

[22] Filed: Jun. 5, 1995

[30] Foreign Application Priority Data

Jun. 27, 1994 [JP] Japan ................................ 6-144406

[51] Int. Cl.[6] ........................................................ G11B 7/09
[52] U.S. Cl. .................................. 369/44.28; 369/44.29; 369/44.37
[58] Field of Search ............................. 369/44.28, 44.37, 369/44.29, 44.35, 44.25, 44.26, 44.34, 44.41

[56] References Cited

U.S. PATENT DOCUMENTS 4,817,073  3/1989  Suzuki .................................. 369/44.28
4,887,253  12/1989  Tateishi et al. ..................... 369/44.28
5,056,074  10/1991  Tateishi et al. ..................... 369/44.28
5,179,545  1/1993  Tanaka et al. ....................... 369/44.29

FOREIGN PATENT DOCUMENTS

61-148636  7/1986  Japan .
63-238539  10/1988  Japan .

*Primary Examiner*—Thang V. Tran
*Attorney, Agent, or Firm*—Ronald P. Kananen

[57] ABSTRACT

A device for inspecting the surface of a disc-shaped recording medium is provided. The inspection device is capable of performing track control unaffected by the widths of the land and the groove in the radial direction of the recording medium in inspecting the entire surface of a data recording region of the recording medium. The device has a spindle motor 1, an optical pickup 2 and a thread motor 3. While an output signal is supplied from a spot size control section 4b within a signal detection unit 4, two sub-beams are radiated from the optical pickup for tracking control. These sub-beams are radiated to the vicinity of the boundary region between the land sandwiched between the grooves where the light volume of the reflected light of the radiated light is minimized.

12 Claims, 10 Drawing Sheets

DEVICE FOR INSPECTING THE SURFACE OF DISC-SHAPED RECORDING MEDIUM

BACKGROUND OF THE INVENTION

This invention relates to a device for inspecting a surface of a disc-shaped recording medium, such as an optical disc or a magneto-optical disc, and, above all, that of a mold used for producing the disc-shaped recording medium, such as a metal master or a stamper, in which the recording medium or the mold has lands and grooves. The device is used in an apparatus for producing the disc-shaped recording medium or the mold.

The disc-shaped recording medium, such as a magnetic disc, which is recorded or reproduced using a slide type recording/reproducing head, is required to have a smooth sliding surface in consideration of performance and durability of the recording/reproducing head. Such a disc-shaped recording medium is in need of surface inspection in the course of a manufacturing process thereof for detecting the possible presence of protuberances on the sliding surface on which slides the recording/reproducing head for providing a basis for judgement as to acceptability thereof as to the above-mentioned surface smoothness.

In surface inspection of the disc-shaped recording medium, the conventional practice has been to check the entire slide surface thereof on which slides the recording/reproducing head with the aid of an optical microscope or a picture processing device for detecting the presence of foreign matter. Although a high inspection capability can be achieved with these methods as to the presence of foreign matter, the information along the height of the foreign matter cannot thereby be obtained.

In the field of the optical disc, inspection with the aid of a laser beam is carried out in addition to visual inspection with the aid of an optical microscope. That is, a laser beam from a laser light source on the order of tens to hundreds of micrometers is converged by a laser light optical system on an optical disc surface and spirally swept thereon for inspecting the recording surface of the optical disc. With this method, since the variation in the light volume is averaged depending on the beam spot size, delicate variations in the minute-sized lands or grooves on the reflecting surface cannot be detected.

There has also been known a surface inspection device for inspecting the surface of the disc-shaped recording medium in which a laser spot, converged to a beam size on the order of several micrometers using the laser optical system, is simply swept in a spiral path for achieving the inspection of the entire surface of the recording medium.

If the surface inspection device for the optical disc-shaped recording medium employing the laser beam optical system is applied to a recording medium having grooves formed thereon, the light volume of the reflected light from the disc surface is changed significantly at a time instant the laser spot traverses the groove and the land respectively representing the recess and the protuberance formed on the disc surface, unless the tracking control is in operation. There may be occasions wherein the variation in the light volume from the lands and grooves on the disc surface becomes invisible. The surface inspection device for the disc-shaped recording medium having such grooves as recesses is in need of tracking control for surface inspection, that is, the laser spot has to be controlled so as to follow the land sandwiched between two grooves as the laser spot is caused to sweep the entire disc surface.

Figure 1:
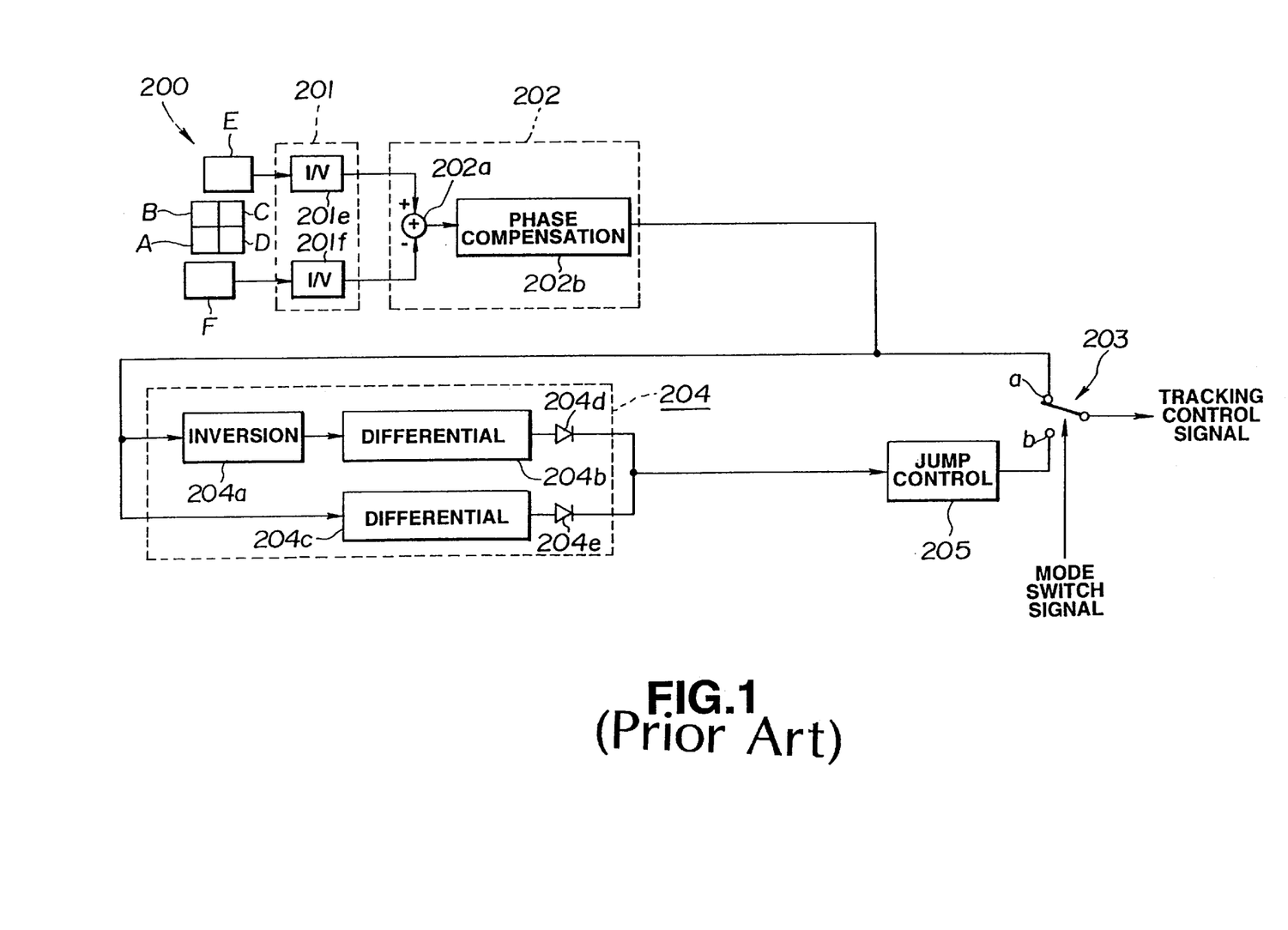
FIG. 1 is a schematic block diagram showing a conventional construction for tracking control.

As shown in JP Laid Open Patent Publication No. JP-A-61-148636, provisionally published on Jul. 7, 1986, such tracking control is a technique commonly adopted with an optical disc. Such tracking control is now explained by referring to a tracking control circuit applied to a stamper inspection device, as shown in FIG. 1.

Figure 2:
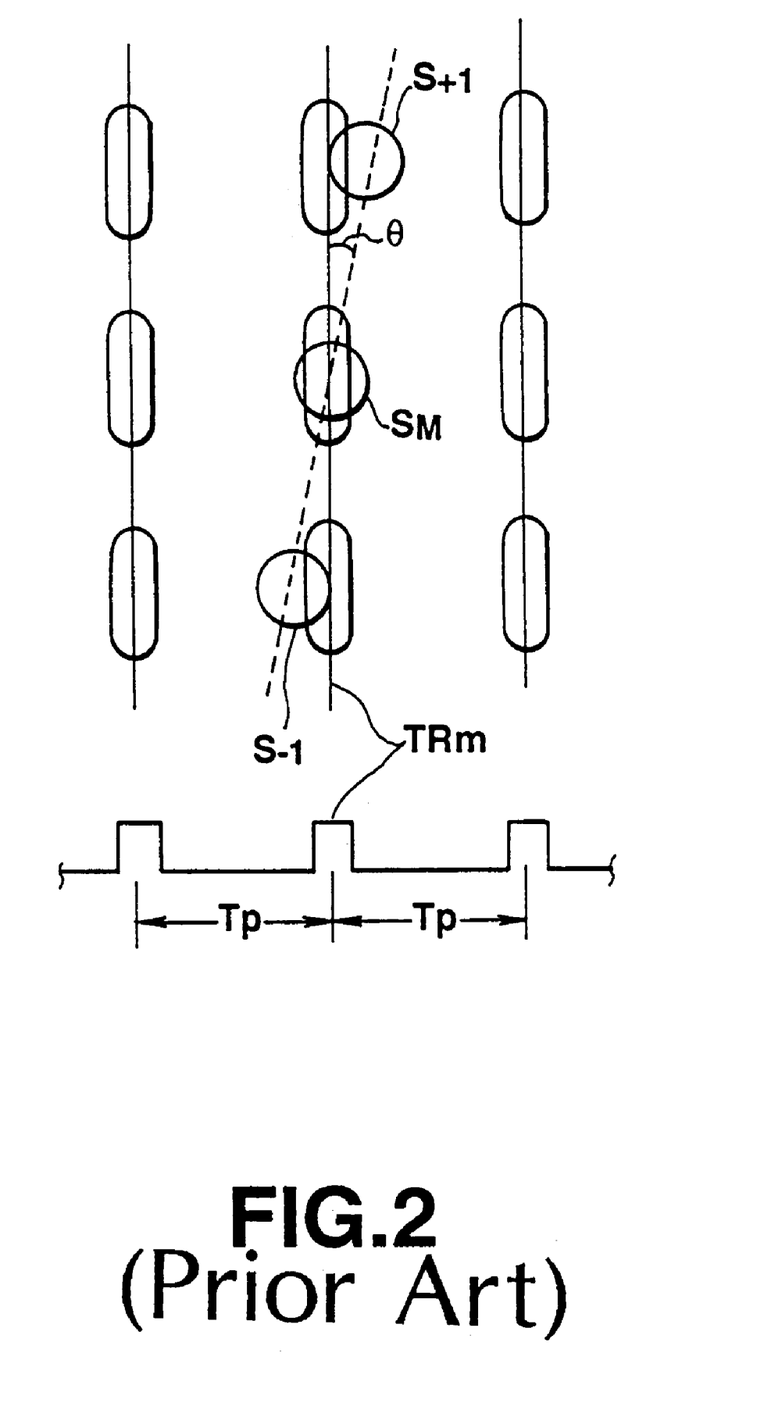
FIG. 2 illustrates an array of three laser spots relative to pits on a conventional optical disc.

In general, a light receiving unit 200 for detecting the light reflected by an optical disc surface has six-segment light receiving elements A to F for receiving the reflected light of a main beam (O'th order light) $S_M$ and two sub-beams (±1st order light). These two sub-beams are made up of a preceding sub-beam (+1st order light) preceding the main beam in its proceeding direction and a follow-up sub-beam (−1st order light) $S_{-1}$ positioned following the main beam. These two sub-beams $S_{+1}$ and $S_{-1}$ are radiated so as to be located on a track inclined by a angle ±θ with respect to a track $TR_m$, as shown for example in FIG. 2.

For tracking control, the light receiving unit 200 employs detection outputs of the light receiving elements E and F, among the six-segment light receiving elements, which are configured to detect the reflected light from the leading sub-beam and the trailing sub-beam. These detection outputs are fed to a current/voltage converter 201. The current/voltage converter 201 includes current/voltage converting circuits 201e, 201f for conversion. The resulting converted signals are fed to a tracking error signal detection circuit 202.

The tracking error signal detection circuit 202 has an adder 202a and a phase compensation circuit 202b. An output signal of the light receiving element E is additively entered to an input of the addition unit 202a, while an output signal of the light receiving element F is subtractively entered to its other input. A tracking error signal is derived from these input signal inputs. The phase compensation circuit 202b performs phase compensation on the tracking error signal and transmits the phase-compensated signal to a fixed terminal a of a mode changeover switch 203. The phase compensation circuit 202b transmits the tracking error signal to a zero-crossing detection unit 204.

The zero-crossing detection unit 204 has an inverting circuit 204a, two differentiation circuits 204b, 204c and two diodes 204d, 204e. The zero-crossing detection unit 204 routes the tracking error signal from the phase compensation circuit 202b to the inverting circuit 204a and to the differentiating circuit 204c. The inverting circuit 204a inverts the signal level of the tracking error signal and transmits the inverted signal to the differentiating circuit 204b. The differentiating circuits 204d, 204c take out only positive terminal side signals as signals indicating the maximum and minimum positions of the supplied signals and transmit the signals to a jump control circuit 205.

The jump control circuit 205 issues an acceleration pulse for track jumping a laser beam spot radiated from e.g., an optical pickup unit, and subsequently transmits a deceleration pulse to the other fixed terminal b of the mode changeover switch 203. The jump control unit 205 also effects timing control in supplying these various pulse signals.

The mode changeover switch 203 is changed over responsive to a mode changeover signal changing over the tracking control mode to the track jump mode and vice versa. The mode changeover switch 203 issues the signals supplied to its fixed terminals as a tracking control signal.

Figure 3A:
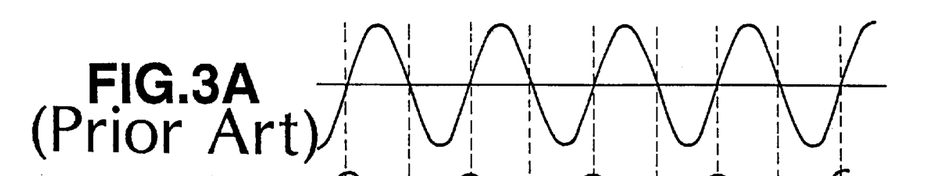
FIGS. 3a to 3d are graphs showing various waveforms of signals produced from pits of a conventional optical disc.
Figure 3B:
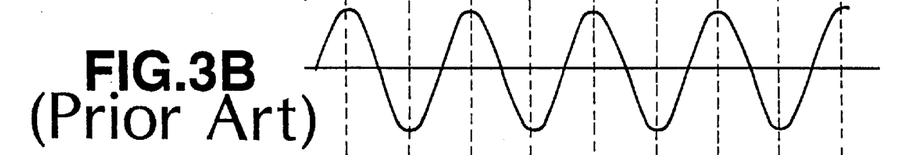
Figure 3C:
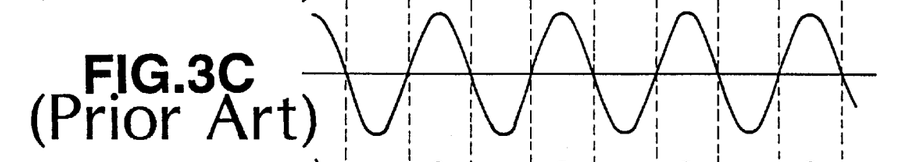
Figure 3D:
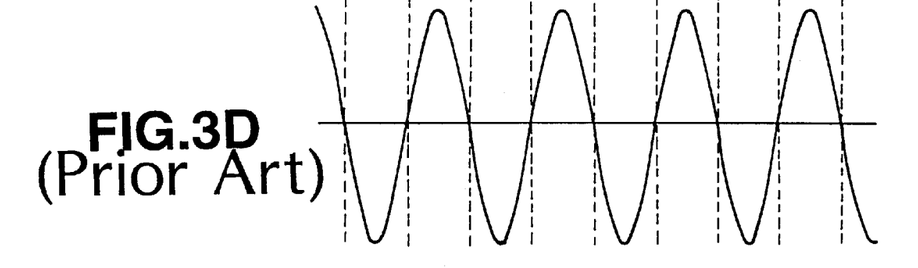

If, with the above constitution, the tracking error signal is found based upon output signals from various parts, an output signal of the light receiving element E responsive to the leading sub-beam $S^{+1}$ as shown in FIG. 3a and an output signal of the light receiving element F responsive to the trailing sub-beam $S^{-1}$ as shown in FIG. 3c are outputted as signals 180 out of phase relative to each other. The output signals of the light receiving elements E and F are respectively entered at the adder 202a additively and subtractively for producing a tracking error signal as shown in FIG. 3d.

This tracking error signal is routed to the zero-crossing detection unit 204. The differentiating circuits 204b, 204c of the zero-crossing detection unit 204 differentiate the signal level of the tracking error signal for detecting the peak of the tracking error signal. The peak position of the tracking error signal represents the zero-crossing position of a high frequency (HF) signal obtained on summing the output signals of the four-segment light receiving elements A, B, C and D, as shown in FIG. 3.

In addition, the zero-crossing detection unit 204 supplies a positive polarity pulse signal to the jump control unit 205 as a zero-crossing signal via diodes 204d, 204e. In the jump control circuit 205, the accelerating pulse impression start timing and the decelerating pulse impression start timing for jumping over plural tracks can be accurately produced based upon the supplied pulse signal.

Figure 4:
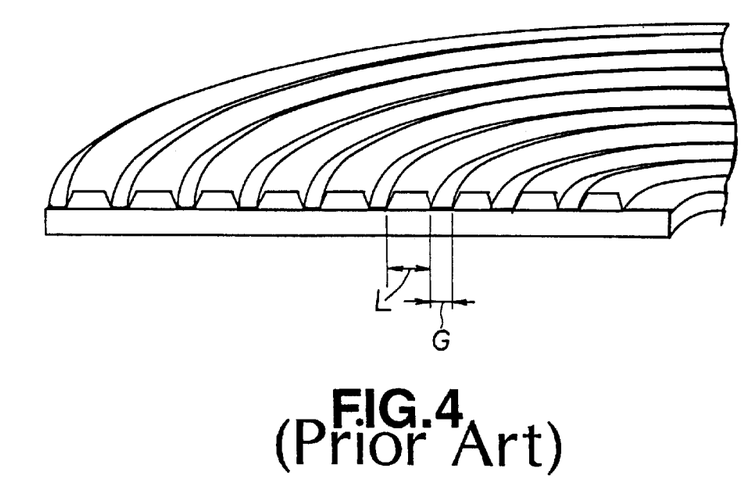
FIG. 4 is a schematic cross-sectional view of a recording medium on which lands and grooves are formed with a nonuniform pitch.

Among disc-shaped recording media, there is such a recording medium in which a convexed portion termed a land has a radial width larger than the laser spot size and a concave portion on the lateral side of the land termed a groove has a radial width substantially equal to the laser spot size, as shown in FIG. 4.

If, with such disc-shaped recording medium, the laser spot traverses a track, the light volume of the reflected light from the disc surface having such lands and grooves is not a repetition of increased light volume and decreased light volume with the reflected light volume from the lands being maximum and the light volume reflected from the grooves being minimum. In effect, the reflected light volume becomes minimum at the land-groove boundary region, and becomes only slightly smaller on the groove than on the land.

The tracking error signal produced on receiving the reflected light from the disc-shaped recording medium is obtained as an irregular waveform signal having a period twice that of the prior-art tracking error signal by setting the land width so as to be unequal to the groove width, such as by setting the land width to groove width ratio to 2:1. If such tracking error signal is employed, it is not possible with the conventional tracking control technique to cause the laser spot to follow the track with sufficiently accuracy.

OBJECT AND SUMMARY OF THE INVENTION

In view of the above-described status of the art, it is an object of the present invention to provide a device for inspecting the surface of a disc-shaped recording medium whereby the entire surface of the data recording area may be inspected by tracking control which remains unaffected by the radial widths of the lands and the grooves.

In one aspect, the present invention provides an apparatus for inspecting a signal surface of a disc-shaped recording medium or a mold employed for producing the disc-shaped recording medium. The apparatus has a laser light source for radiating a laser beam, laser beam splitting means for splitting the laser beam radiated from the laser light source into a main beam and first and second sub-beams, and an optical system for radiating the main beam and the first and second sub-beams to the disc-shaped recording medium or the mold and for separating the reflected light beam from the disc-shaped recording medium or the mold from the radiated laser beam. The apparatus also has converting means for converting the reflected sub-beams from the optical system into first and second electrical signals, and tracking control signal generating means. The tracking control signal means has means for calculating a tracking error signal from the first and second electrical signals outputted by the converting means, means for detecting only a position corresponding to a track edge of the disc-shaped recording medium or the mold from the tracking error signal for generating a position signal, and means for generating a track jump signal for commanding the desired number of track jumps from the position signal. The tracking signal generating means outputs a track jump signal as a tracking control signal. The apparatus also has means for causing the laser light source to follow the track on the recording medium or the mold based on the tracking control signal.

In another aspect, the present invention provides a method for inspecting a signal surface of a disc-shaped recording medium or a mold employed for producing the disc-shaped recording medium. The method includes the steps of splitting a laser beam radiated from a laser light source into a main beam and first and second sub-beams, radiating the main beam and the first and second sub-beams to the disc-shaped recording medium or the mold and separating the reflected light beam from the disc-shaped recording medium or the mold from the radiated laser beam. The method also includes the steps of converting the reflected sub-beams from the optical system into first and second electrical signals, calculating a tracking error signal from the first and second electrical signals outputted by the converting means and detecting only a position corresponding to a track edge of the disc-shaped recording medium or the mold from the tracking error signal for generating a position signal and for generating a track jump signal for commanding the desired number of track jumps from the position signal. The method also includes the steps of outputting the track jump signal as a tracking control signal, and causing the laser light source to follow the track on the recording medium or the mold based on the tracking control signal.

The land (track) has a width approximately twice the width of the groove (guard band).

The spot size control section has a level comparator for comparing the signal level of the detected tracking error signal and a constant pre-set signal level, a locally maximum/locally minimum detector for detecting the locally maximum position or the locally minimum position of the tracking error signal, and a pulse selector for selecting an output signal of the locally maximum/locally minimum detector responsive to a control signal from the level comparator.

The two sub-beams are arrayed in the vicinity of the boundary regions between the land and the grooves for detecting the direction of the deviation of the sub-beams with respect to the track center. The deviation is corrected for causing the main beam to stably follow the track center.

With the device for inspecting the surface of the disc-shaped recording medium according to the present invention, the two sub-beams are arrayed in the vicinity of the boundary region between the land and the grooves, where the light volume of the reflected light becomes minimum, for detecting the direction of the deviation of the sub-beams relative to the track center. Such deviation is corrected for causing the main beam to stably follow the track center.

The pulse selector of the spot size controlling unit is fed with pulses generated responsive to locally maximum or locally minimum positions as detected in the tracking error signal. The pulse selector is also fed with a control signal when the signal level of the tracking error signal detected by the level comparator is higher than a constant pre-set level in order to control the timing of the acceleration pulse and the deceleration pulse outputted during track jump control of the optical pickup.

DESCRIPTION OF THE PREFERRED EMBODIMENT

Referring to the drawings, a preferred embodiment of the present invention will be explained in detail. In the present embodiment, the inspection device of the present invention is applied to surface inspection of a grooved optical disc, referred to herein simply as an optical disc.

Figure 5:
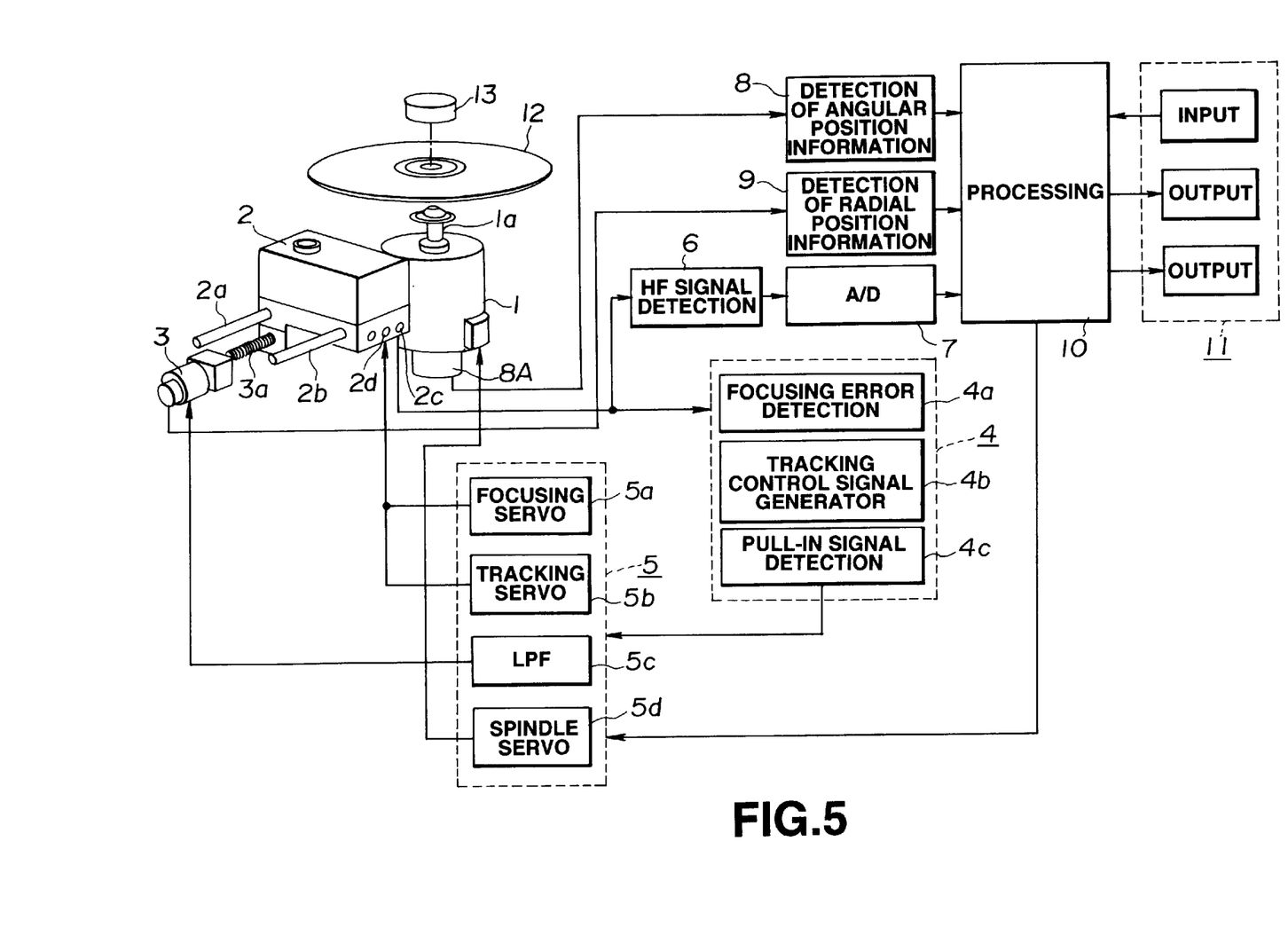
FIG. 5 is a schematic block diagram of a device for inspecting the surface of a disc-shaped recording medium according to the present invention, as applied to inspection of an optical disc surface.

Referring to FIG. 5, the inspection device for inspecting the optical disc surface has a spindle motor 1, an optical pickup unit 2 and a thread motor 3. In addition, the inspection device has a signal detection unit 4, a servo unit 5, a high-frequency (HF) signal detection unit 6, an A/D converter 7, an angular position information detection circuit 8, a radial position information detection circuit 9, an arithmetic-logical unit 10 and an input/output unit 11.

The spindle motor 1 is secured to a turntable 1b via a rotary shaft 1a. An optical disc 12 to be inspected is set on the turntable 1b. An optical disc retainer 13 acts on the optical disc 12 for thrusting it towards the turntable 1b for rotating the optical disc 12 kept in such setting state. The spindle motor 1 has an angular position detection unit 8A on its lower portion as e.g., an encoder.

The optical pickup unit 2 is arranged below the optical disc 12 set on the turntable 1b. The optical pickup unit 2 is configured to be movable radially in relation to the optical disc 12. Such movement of the optical pickup occurs as a horizontal translatory movement. Thus the optical pickup unit 2 is moved along two horizontal guides 2a, 2b. To the optical pickup unit 2 is supplied a rotational force of the thread motor 3 by a translatory movement unit via a tapped shaft 3a.

The optical pickup unit 2 includes a laser generating unit, not shown herein, and an optical system, also not shown herein, for radiating an outgoing light of the laser generating unit via an objective lens to the surface of the optical disc 12 and for detecting the reflected light from the surface of the optical disc 12. The optical pickup unit 2 transmits the reception light output via a terminal 2c to the signal detection unit 4 and to the HF signal detection unit 6. The construction of the optical pickup is disclosed in, for example, U.S. Pat. No. 4,912,693.

The angular position information detection unit 8A, provided at a lower portion of the spindle motor 1, transmits a detection output to the angular position information detection circuit 8. The angular position information detection circuit 8 transmits the angular position information to the arithmetic-logical unit 10.

The thread motor 3 causes translatory movement of the optical pickup unit 2 along the guides 2a, 2b by rotation of the thread motor 3. The radial position information detection circuit 9 detects the amount of translatory movement by a signal derived from the thread motor 3 detecting the amount of translatory movement of the optical pickup unit 2, and transmits the position information of the objective lens of the optical pickup unit 2 along the radius of the optical disc 12 to the arithmetic-logical unit 10.

The optical pickup unit 2 transmits detection signals from the four-segment light receiving elements to the HF signal detection unit 6 as detection outputs. The HF signal detection unit 6 outputs the detected HF signals to the A/D converter 7. The A/D converter 7 transmits the digital signal converted from the HF signal to the arithmetic-logical unit 10.

The arithmetic/logical unit 10 performs arithmetic-logical operations based upon the various sorts of the information supplied as above and from the input/output unit 11 and transmits control signals to, for example, a spindle servo circuit 5d of the servo unit 5 as later explained. The construction of the arithmetic-logical unit 10 will be explained subsequently.

The signal detection unit 4 is made up of a focusing error detection section 4a, a spot size control section 4b and a pull-in signal detection section 4c. For detecting various sorts of signals, signals detected based upon the light receiving outputs are routed to the servo unit 5. The various circuits will be explained subsequently.

The servo unit 5 has a focusing servo circuit 5a, a tracking servo circuit 5b, a low-pass filter (LPF) circuit 5c and a spindle servo circuit 5d. In the servo unit 5, the focusing servo circuit 5a, a tracking servo circuit 5b and a low-pass filter (LPF) circuit 5c output driving control signals responsive to an output signal of the signal detection unit 4. The focusing servo circuit 5a and the tracking servo circuit 5b transmit driving control signals to the optical pickup 2 via a terminal 2d. The LPF circuit 5c transmits the driving control signal to the thread motor 3. The spindle servo circuit 5d transmits a driving control signal responsive to the output signal of the arithmetic-logical unit 10 to the spindle motor 1. These circuits will be explained subsequently.

The device for inspecting the optical disc surface, having the above construction, inspects the surface of the optical disc 12, based upon the information derived from the optical pickup unit 2, while controlling the optical pickup unit 2.

The circuit construction of various portions of the present inspection device will be explained by referring to the schematic block diagrams of FIG. 6 to 9.

Figure 6:
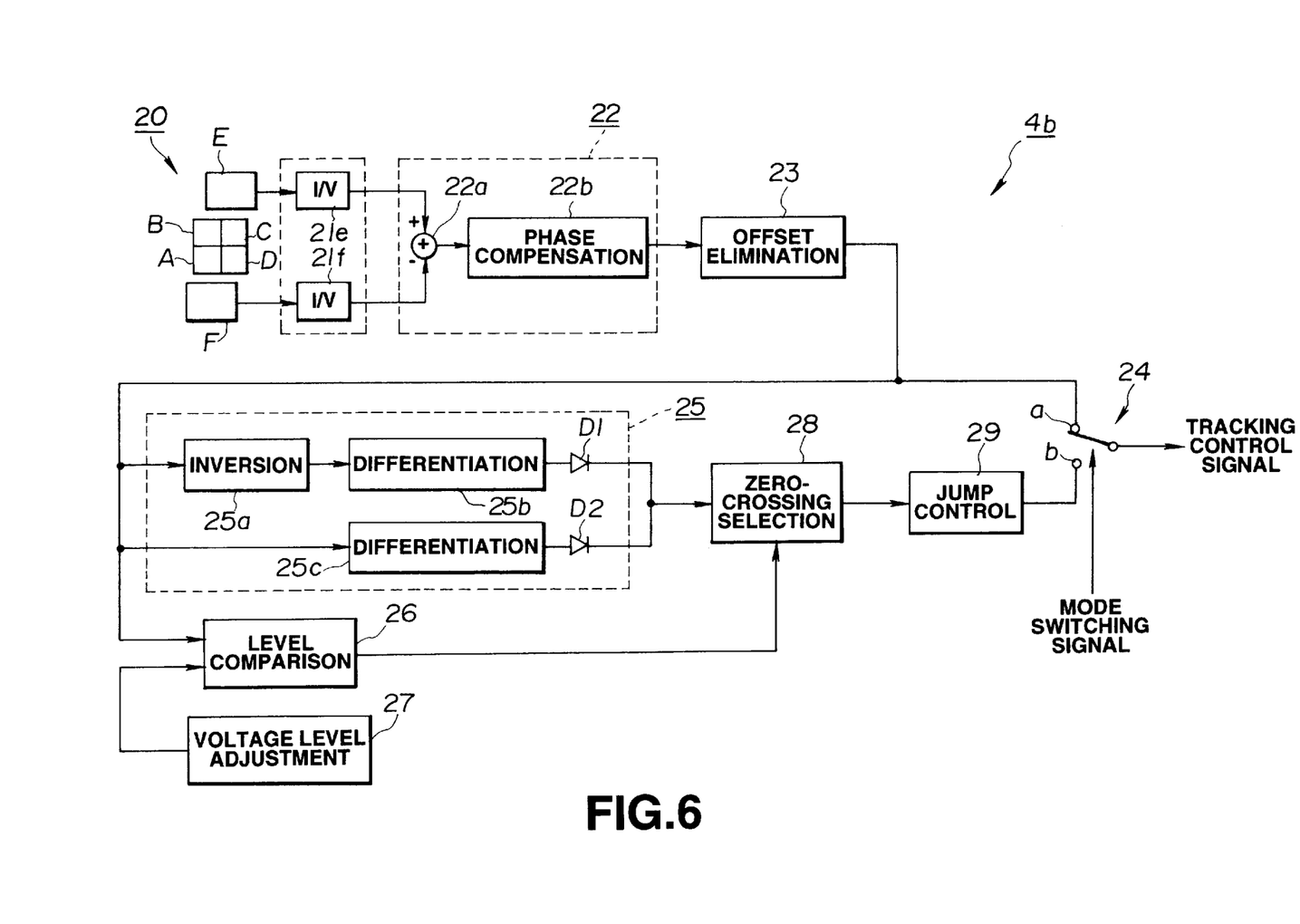
FIG. 6 is a schematic block diagram showing tracking control with the inspection device shown in FIG. 5.

The tracking control signal generating section 4b generates a tracking control signal for the laser spot responsive to the signal mode based upon the detected signal. The tracking control responsive to the mode includes usual laser spot follow-up control relative to the track of the optical disc 12 and track jump control causing high-speed movement of the optical pickup 2 across one or more tracks. Such track jump control includes special-mode inspection such as inspecting the surface of the same track a plural number of times by repeating a 1-track jump by the above-mentioned track jump control.

The block construction of the spot size control section 4b for effecting such control is shown in FIG. 6.

The tracking control signal generating section 4b receives the light from an optical system by light receiving elements E and F of the six-segment light receiving elements A to F of a light receiving section 20 and transmits output signals of I/V converting circuits 21e, 21f of a current/voltage converting section 21 to a tracking error signal detection section 22.

The tracking error signal detection section 22 is made up of an adder 22a and a phase compensation circuit 22b. A signal derived from the light receiving element E and a signal derived from the light receiving element F are respectively entered to one terminal and the other terminal of the adder 22a additively and subtractively. An output signal of the adder 22a is transmitted to the phase compensation circuit 22b. Thus the tracking error signal detection unit 22 transmits the phase-compensated tracking error signal to an offset elimination circuit 23 configured for eliminating offset components contained in the tracking error signal. The offset eliminating circuit 23 may be provided upstream of the tracking error signal detection section 22.

The waveforms shown in FIG. 11 are close to ideal waveforms, hence phase deviation or offset components are not shown therein. In effect, there may be occasions wherein it becomes necessary to perform phase compensation and elimination of the offset components.

The offset eliminating circuit 23 transmits the tracking error signal to a fixed terminal a of a mode changeover switch 24, a zero-crossing signal detection section 25 and a level comparator 26.

The zero-crossing signal detection section 25 includes an inverter circuit 25a, differentiating circuits 25b, 25c and diodes D1, D2. The zero-crossing signal detection section 25 inverts a negative-polarity signal by an inverting circuit 25a to form a corresponding positive-polarity signal. The detection section also generates pulse signals corresponding to the maximum or locally maximum positions of the positive-polarity signal by the differentiating circuits 25b, 25c and transmits the resulting signals through diodes D1, D2 in order to take out only the positive polarity side pulse signals. The zero-crossing signal detection section 25, having the above construction, outputs the locally maximum point, locally minimum point and the point of inflection (alternatively, the maximum or minimum point) as pulse signals to a zero-crossing selection circuit 28.

The tracking error signal and a voltage adjusted by a voltage adjustment section 27 are entered to one and the other inputs of the level comparator 26, respectively. When the absolute value of the signal level of the tracking error signal becomes larger than the adjusted voltage level, the level comparator 26 outputs a zero-crossing selection signal to the zero-crossing selection circuit 28.

In such case, the zero-crossing selection circuit 28 selects only the pulse signals, among the pulse signals from the zero-crossing signal detection section 25, which indicate the true maximum and minimum positions, and transmits the selected signals to a jump control section 29. The jump control section generates acceleration and deceleration pulses, based upon the pulse signals from the zero-crossing selection circuit 28, in order to effect control responsive to the number of tracks to be jumped over. The jump control section 29 transmits the output signals to the opposite side terminal b of the mode changeover switch 24.

The acceleration pulse outputting timing may also be set to a time point when the signal level as later explained and shown for example in FIG. 11h reaches a level "H".

The mode changeover switch 24 is changed over responsive to a mode changeover signal derived from signal detected by e.g., a CPU designed for controlling the device.

By controlling the signal switching in this manner, a tracking control signal for causing the objective lens of the optical pickup to correctly follow the track of the optical disc 12 is outputted to the servo unit 5.

Figure 7:
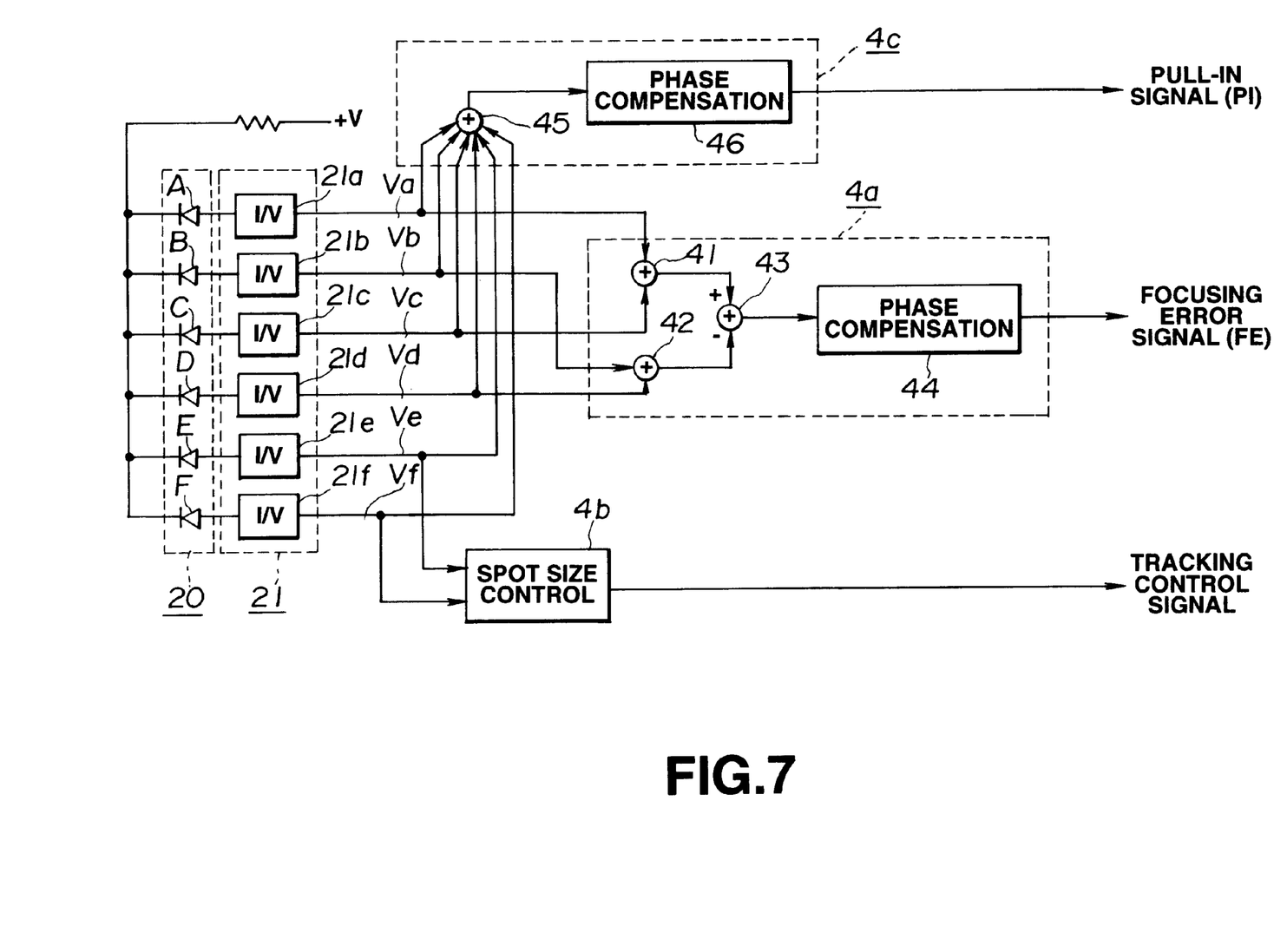
FIG. 7 is a schematic block diagram showing a signal generating unit for generating various signals in the inspection device shown in FIG. 5.

The circuit construction for generating signals required for controlling the optical disc surface inspection device, for example, the pull-in signal or the focusing error signal, will be explained by referring to FIG. 7.

Detection signals of the six light receiving elements A to F of the light receiving section 20 are routed to I/V converting circuits 21a to 21f of the current/voltage converting section 21 so as to be converted into signals proportionate to the voltage Va, Vb, Vc, Vd, Ve and Vf. These signals are issued as output signals.

For generating the pull-in signals, four Va, Vb, Vc and vd of these six signals are routed to an adder 45 of the pull-in signal detection section 4c. The output signal of the adder 45 is routed to a phase compensating circuit 46 which then outputs a phase-compensated pull-in signal.

For generating the focusing error signal, the signals Va and Vc are routed to an adder 41 of the focusing error signal detection section 4a. The signals Vb and Vd are routed to an adder 42 of the focusing error signal detection section 4a. The results of addition of the adders 41 and 42 are respectively supplied to an adder 43 additively and subtractively. An output signal of the adder 43 is routed to a phase compensation circuit 44 which then effects phase compensation on the output signal of the adder 43 and outputs the resulting phase-compensated signal as the focusing error signal.

Figures 8A, 8B:
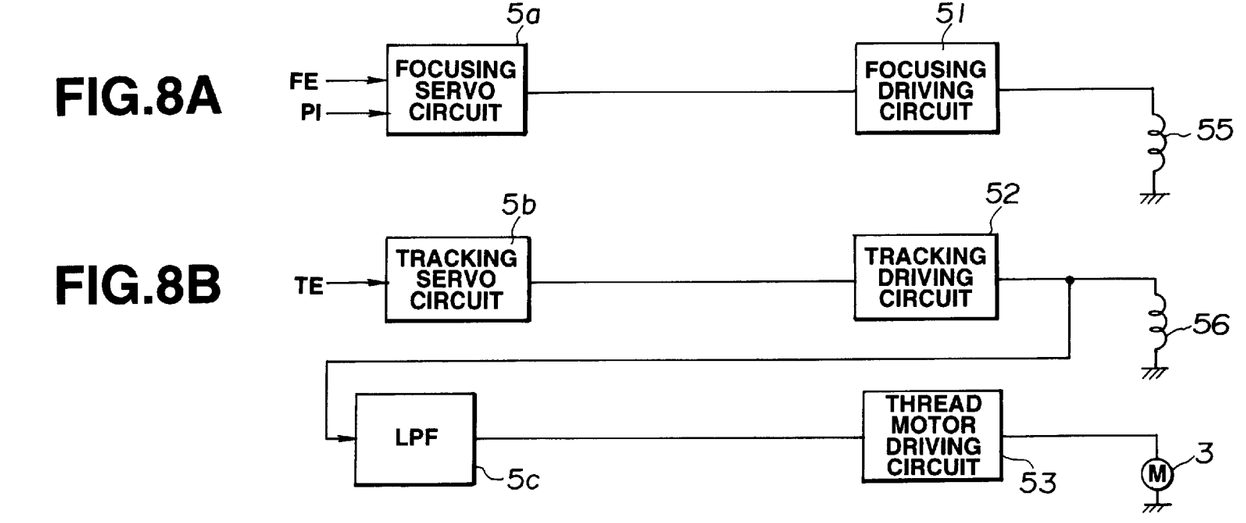
FIG. 8 comprised of FIGS. 8A, 8B, and 8C, is a schematic block diagram showing a servo unit in the inspection device shown in FIG. 5.
Figure 8C:
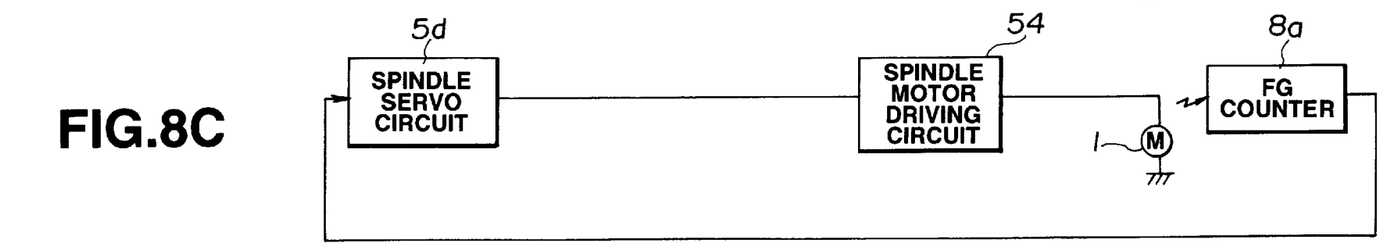

The servo unit 5 is configured as shown in FIG. 8.

The servo unit 5 is fed with the tracking control signal TE, inclusive of the track jump signal detected by the signal detection unit 4, the focusing error signal FE and the pull-in signal PI. The servo unit 5 is also fed with the output signal of the arithmetic-logical unit 10 as a control signal for e.g., the position information.

Based upon the input focusing error signal and pull-in signal, the focusing servo circuit 5a routes the focusing control signal to a focusing driving circuit 51. The focusing driving circuit 51 outputs a driving signal required for driving the focusing coil 55 for effecting an adjustment for optimizing the focusing.

The tracking servo circuit 5b routes the input tracking control signal TE to a tracking driving circuit 52. The tracking driving circuit 52 outputs a tracking driving signal required for driving a tracking coil 56 of the objective lens of the optical pickup for effecting an adjustment for optimizing the tracking. The tracking driving circuit 52 routes the tracking driving signal to the LPF circuit 5c. The tracking driving signal is fed via the LPF circuit 5c to a thread motor driving circuit 53. The thread motor driving circuit 53 outputs a thread motor driving signal required for driving the thread motor 3 for effecting rough position adjustment of the optical pickup 2 relative to the optical disc 12.

The tracking servo circuit 5b may be configured to route the tracking control signal from the tracking control signal generating circuit 4b and a signal inverted from the tracking control signal by an inverting amplifier, not shown, to one and the opposite side terminals of a changeover switch, not shown, respectively, and to transmit an output signal of the changeover switch to the tracking coil 56 via an amplifier, also not shown.

A detection output of a FG counter 8a, as an angular position sensor for detecting the rotational state of the spindle motor 1, is routed to the spindle servo circuit 5d, as shown in FIG. 5. The spindle servo circuit 5d is responsive to a rotational output of the spindle motor 1 to transmit a spindle control signal to a spindle motor driving circuit 54. The spindle motor 54 outputs a spindle motor driving signal required for driving the spindle motor 1 for controlling its rotation.

Figure 9:
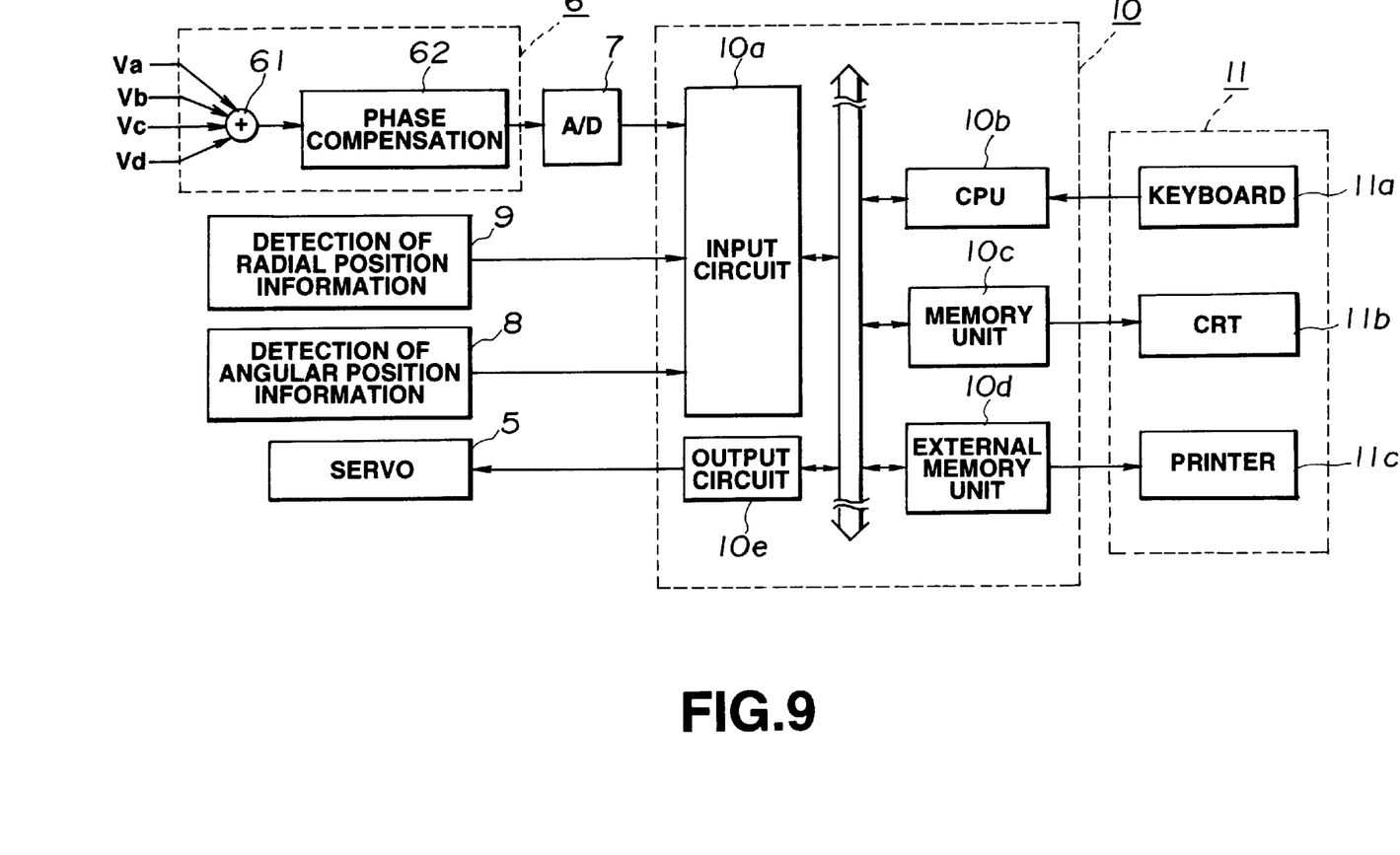
FIG. 9 is a schematic block diagram showing an HF signal detection unit and an arithmetic-logical unit in the inspection device shown in FIG. 5.

Referring to FIG. 9, detection of the HF signal and detection of the information required for operational control will be explained.

The four voltage level signals Va to Vd, detected by the light receiving areas of the four-segment light receiving elements, are additively entered to an adder 61 of the HF signal detection unit 6. The adder 61 outputs the result of addition to a phase compensation circuit 62, which then outputs a phase-compensated HF signal to the A/D converter 7. The A/D converter 7 converts the HF signal into a digital signal which is routed to the arithmetic-logical unit 10.

The information required for operational control of the optical disc surface inspection device is supplied to the arithmetic-logical unit 10, which is fed with an output signal of the radial position information detection circuit 9 made up at least of a linear scale, a dedicated amplifier and a position information digital output circuit, not shown.

The arithmetic-logical unit 10 is also fed with an output signal of the angular position information detection unit 8 made up at least of an encoder, a counter and an angular position information digital circuit, also not shown.

The arithmetic-logical unit 10 receives the above-mentioned various signals as the information via its internal input circuit 10a. The input circuit 10a transmits the information to an enclosed CPU 10b, a memory 10c and an external memory 10d over an internal data bus DB. The CPU 10b, memory 10c and the external memory 10d exchange the signal or data over the internal data bus DB. The arithmetic-logical unit 10 also receives a signal from a keyboard 11a or transmits a signal to a CRT 11b or a printer 11c. The keyboard 11a, the CRT 11b and the printer 11c as well as other units, not shown, are included in the input/output unit 11. The arithmetic-logical unit 10 also outputs a signal to the servo unit 5 via an output circuit 10e.

The operation of the optical disc surface inspection device according to the present invention will be explained by referring to FIGS. 10 and 11.

Figures 10A, 10B:
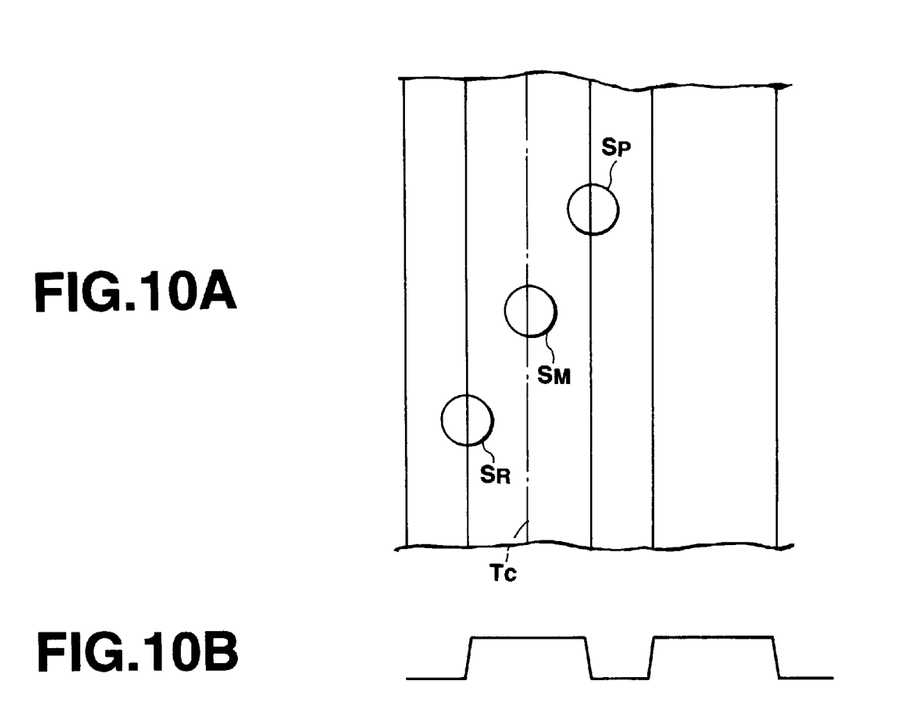
FIGS. 10a and 10b schematically illustrates an array of laser spots on an optical disc being inspected by the inspection device shown in FIG. 5 and the optical disc surface.

FIG. 10a shows a portion of the optical disc 12, on the surface of which a groove (guard band) and a land (track) have been formed, and laser spots radiated on the disc surface via an objective lens. When viewed in a cross-sectional view taken along the radius of the optical disc 12, the land has a width approximately twice the width of the groove, as shown in FIG. 10b. Specifically, the optical disc shown in the cross-sectional view of FIG. 10b has the land width equal to 3.2 µm and the groove width equal to 1.6 µm.

The optical disc surface inspection device radiates laser light so that a main beam $S_M$ is arrayed at a track center position Tc and a sub-beam $S_P$ preceding the main beam $S_M$ and a sub-beam $S_R$ succeeding the main beam $S_M$ are arrayed at two boundary regions of the land. The beam array is pre-set prior to inspection. More specifically, the sub-beams are arrayed in the regions near the boundary between the land and the groove for which the reflected light volume is minimized.

The distance between the center of the main beam $S_M$ and the center of the sub-beams $S_P$ or $S_R$ is approximately 20 µm. Such distance governs the angle the two sub-beams have relative to the track center.

If the optical system of the optical disc surface inspection device is adjusted in this manner and the laser beams are radiated on the optical disc, the light receiving section 20 of the inspection device outputs a waveform as shown in FIG. 11. This waveform represents waveform changes with lapse of time when the laser beam is moved on the optical disc 12 in the left-right direction, that is along the track direction.

Figure 11A:
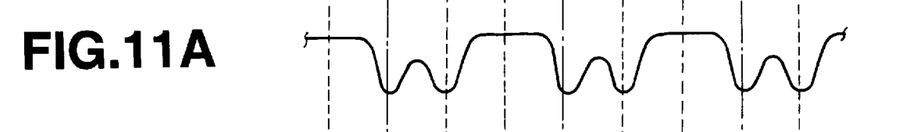
FIGS. 11a to 11i are timing charts for illustrating the waveform and the timing of the output signal of the inspection device shown in FIG. 5.
Figure 11B:
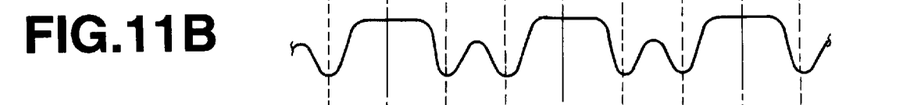
Figure 11C:
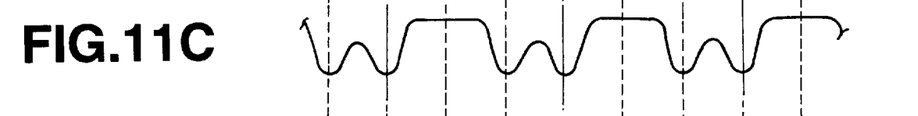
Figures 11D, 11E:
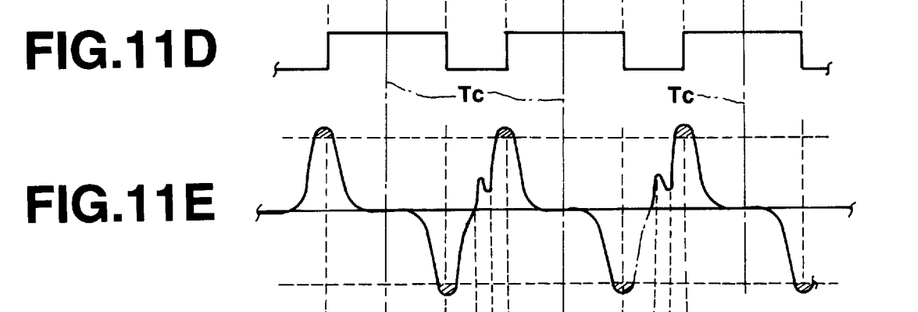

The waveforms of FIG. 11a and 11c show outputs of the light-receiving elements E and F for the leading sub-beam $S_P$ and the trailing sub-beam $S_R$, respectively. The waveform of FIG. 11b shows an output when the main beam $S_M$ is received by the four light receiving elements A to D. For illustrating these output waveforms and the land and the groove of the optical disc 12, FIG. 11d shows a portion of the optical disc 12. The tracking error signal shown in FIG. 11e is obtained by subtracting the waveform of FIG. 11c from the waveform of FIG. 11a. With the present optical disc surface inspection device, tracking servo is effected, using the tracking error signal, so that the main beam $S_M$ is perpetually at the track center of the optical disc 12 in order to permit the laser spot to stably follow the desired track.

The tracking error signal is simultaneously supplied to the zero-crossing signal detection unit 25. In effecting track jump, basically the mode changeover switch 24 is changed over with the present optical disc surface inspection device based upon the zero-crossing position of the tracking error signal. It suffices to effect mode switching at the zero-crossing position whilst the signal level assumes the constant zero value for a pre-set time duration. Such mode switching is made by detecting such position using a logical output when the signal levels of FIG. 11a and 11c both assume the minimum value, as shown in FIG. 11h.

Figure 11F:
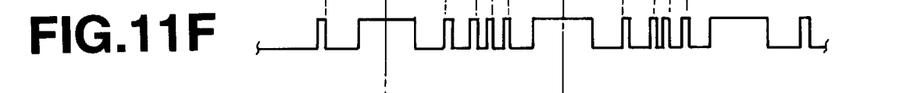

The tracking error signal supplied to the zero-crossing signal detection unit 25 is susceptible to inundations due to the pitch difference between the land and the groove, as shown in FIG. 11e. If this tracking error signal is supplied to a zero crossing signal detection section 25, plural pulse signals as shown in FIG. 11f are produced. If the plural pulse signals are generated, it cannot be known at the time of track jump at which pulse signal timing the acceleration pulse is impressed or at which pulse signal timing the deceleration pulse is impressed. Thus it is necessary to select only the required pulse signals. For effecting such selection, an absolute value voltage which represents a threshold voltage with respect to the voltage level of the supplied tracking error signal is supplied from the voltage level adjustment circuit 27 to the level comparator 26.

Figure 11G:
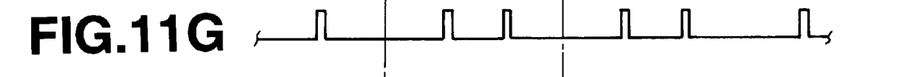
Figure 11H:
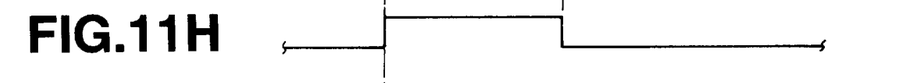

The level comparator 26 outputs a selection signal to the zero-crossing selection circuit 28 when supplied with the tracking error signal exceeding the absolute voltage value. By selecting the pulse signals in this manner, the zero-crossing selection circuit 28 outputs two pulse signals between the center position of a given track and that of an adjacent track, as shown in FIG. 11g.

Figure 11I:
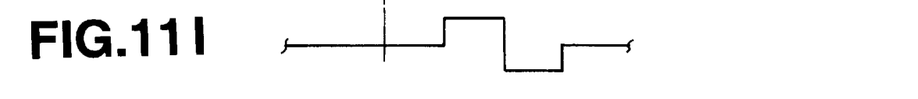

For example, in effecting the track jump control for one-track jump, the jump control section 29 outputs an acceleration pulse by the first pulse signal outputted by the zero-crossing selection circuit 28, while outputting a deceleration pulse by the next pulse signal, as shown in FIG. 11i.

By effecting track jump control responsive only to the thus selected pulse signal, stable track jump control can be achieved even with the use of an optical disc 12 having unequal land and groove pitches.

By the above construction and operation, the laser spot can be caused to stably follow the track center position even though the optical disc surface has lands and grooves and the pitches of the lands and grooves are different in the radial direction.

In addition, since the above construction enables stable track jump control, it becomes possible to produce a signal from a desired position when such particular position is to be inspected repeatedly during inspection of the optical disc surface, thereby improving reliability of the inspection device.

Although the foregoing description has been made with reference to inspection of the optical disc surface, the present invention is not to be limited to the specific embodiment. Thus a highly reliable surface inspection device may be provided by employing a construction similar to that described above for a grooved disc-shaped recording medium employing a discrete track recording system, such as a magneto-optical disc.

What is claimed is:

1. An apparatus for inspecting a signal surface of a disc-shaped recording medium or a mold employed for producing the disc-shaped recording medium, comprising:
   a laser light source for radiating a laser beam,
   a laser beam splitting means for splitting the laser beam radiated from said laser light source into a main beam and first and second sub-beams,
   an optical system for radiating said main beam and said first and second sub-beams to said disc-shaped recording medium or said mold and separating the main beam and first and second sub-beams reflected from the disc-shaped recording medium or said mold from said radiated laser beam,
   converting means for converting the reflected sub-beams from said optical system into first and second electrical signals,
   tracking control signal generating means having means for calculating a tracking error signal from said first and second electrical signals outputted by said converting means, means for detecting only a position corresponding to a track edge, which is the boundary between the track and an adjacent guard band, of said disc-shaped recording medium or said mold from said tracking error signal to produce a position signal, and means for generating a track jump signal for commanding the desired number of track jumps from said position signal, said tracking control signal generating means outputting said track jump signal as a tracking control signal, and
   servo means for causing said laser light source to follow the track on said recording medium or said mold based on said tracking control signal, wherein said means for detecting only the track edge position for generating the position signal comprises means for changing or converting the positions of extreme points of said tracking error signal as pulse signals, and means for selecting only a pulse signal corresponding to the extreme point exceeding a pre-set voltage value as a position corresponding to the track edge position.

2. The apparatus as claimed in claim 1, further comprising:
   switching means for selecting one of the tracking error signal and said track jump signal based upon a changeover signal supplied from outside and outputting the selected signal as said tracking control signal.

3. The apparatus as claimed in claim 1, wherein said means for calculating the tracking error signal finds a difference between said first and second electrical signals and phase-compensates said difference to calculate said tracking error signal.

4. The apparatus as claimed in claim 1, wherein said means for generating said track jump signal generates an acceleration signal at a timing of said pulse signal corresponding to an outer peripheral edge portion of track followed at a current time point and generating a deceleration signal at a timing of a pulse signal corresponding to an inner peripheral edge of a track which is a destination of track jump.

5. The apparatus as claimed in claim 1, wherein said first and second sub-beams are arrayed at positions in vicinity of a boundary between a track and a guard band of the disc-shaped recording medium which minimizes the light volume of the reflected light.

6. The apparatus as claimed in claim 5, wherein said track has a width approximately twice the width of the guard band.

7. A method for inspecting a signal surface of a disc-shaped recording medium or a mold employed for producing the disc-shaped recording medium, comprising the steps of
   splitting a laser beam radiated from a laser light source into a main beam and first and second sub-beams,
   radiating said main beam and said first and second sub-beams to said disc-shaped recording medium or said mold and separating a main beam and first and second sub-beams reflected light beam from the disc-shaped recording medium or said mold from said radiated laser beam,
   converting reflected sub-beams from said optical system into first and second electrical signals,
   calculating a tracking error signal from said first and second electrical signals outputted by said converting means, detecting only a position corresponding to a track edge of said disc-shaped recording medium or said mold from said tracking error signal for generating a position signal,
   detecting only a position corresponding to a track edge, which is the boundary between the track and an adjacent guard band, of said disc-shaped recording medium or said mold from said tracking error signal for generaging a position signal,
   generating a track jump signal for commanding the desired number of track jumps from said position signal, outputting said track jump signal as a tracking control signal, and
   causing said laser light source to follow the track on said recording medium or said mold based on said tracking control signal, wherein said step for detecting only the track edge position for generating the position signal comprises a step for changing or converting the positions of extreme points of said tracking error signal as pulse signals, and a step for selecting only a pulse signal corresponding to the extreme point exceeding a pre-set voltage value as a position corresponding to the track edge position.

8. The method as claimed in claim 7, further comprising the step of selecting one of the tracking error signal and said track jump signal based upon a changeover signal supplied from outside and outputting the selected signal as said tracking control signal.

9. The method as claimed in claim 7, wherein said step of calculating the tracking error signal finds a difference between said first and second electrical signals and phase-compensates said difference to calculate said tracking error signal.

10. The method as claimed in claim 7, wherein said step for generating said track jump signal generates an acceleration signal at a timing of said pulse signal corresponding to an outer peripheral edge portion of a track followed at the current time point and generating a deceleration signal at a timing of the pulse signal corresponding to the inner peripheral edge of a track which is a destination of track jump.

11. The method as claimed in claim 7, wherein said first and second sub-beams are arrayed at the positions in the vicinity of the boundary between the track and the guard band of a disc-shaped recording medium which minimizes the light volume of the reflected light.

12. The method as claimed in claim 11, wherein said track has a width approximately twice the width of the guard band.

* * * * *

UNITED STATES PATENT AND TRADEMARK OFFICE
CERTIFICATE OF CORRECTION

PATENT NO. : 6,002,656
DATED : December, 14, 1999
INVENTOR(S) : MIYAGAWA et al.

It is certified that error appears in the above-identified patent and that said Letters Patent is hereby corrected as shown below:

Column 12, line 60 and 61., claim 7, line 23 and 24, "for generaging a position signal" should read; - - for generating a position signal- -.

Signed and Sealed this

Tenth Day of April, 2001

Attest:

NICHOLAS P. GODICI

Attesting Officer     Acting Director of the United States Patent and Trademark Office